United States Patent
Park et al.

(10) Patent No.: US 10,675,365 B2
(45) Date of Patent: Jun. 9, 2020

(54) CURCUMIN DERIVATIVE, METHOD FOR PRODUCING SAME, AND PHOTO-ACOUSTIC IMAGING AGENT COMPRISING SAME FOR DETECTING BETA-AMYLOID PLAQUE

(71) Applicant: Korea Atomic Energy Research Institute, Daejeon (KR)

(72) Inventors: Yong-Dae Park, Jeollabuk-do (KR);
Jung-Joon Min, Gwangju (KR);
Seung-Dae Yang, Jeollabuk-do (KR);
Min-Goo Hur, Gyeonggi-do (KR);
Seung-Jin Jung, Jeollanam-do (KR);
Yeong-Jin Hong, Gwangju (KR);
Seung-Hwan Park, Gwangju (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 16/337,184

(22) PCT Filed: Sep. 29, 2016

(86) PCT No.: PCT/KR2016/010878
§ 371 (c)(1),
(2) Date: Mar. 27, 2019

(87) PCT Pub. No.: WO2018/062588
PCT Pub. Date: Apr. 5, 2018

(65) Prior Publication Data
US 2019/0224344 A1 Jul. 25, 2019

(51) Int. Cl.
| | |
|---|---|
| A61K 49/04 | (2006.01) |
| A61K 31/69 | (2006.01) |
| A61K 36/9066 | (2006.01) |
| G01N 33/68 | (2006.01) |
| C07F 5/02 | (2006.01) |
| A61K 49/00 | (2006.01) |
| A61K 49/22 | (2006.01) |

(52) U.S. Cl.
CPC .............. A61K 49/04 (2013.01); A61K 31/69 (2013.01); A61K 36/9066 (2013.01); A61K 49/0021 (2013.01); A61K 49/22 (2013.01); C07F 5/02 (2013.01); G01N 33/6896 (2013.01); G01N 2800/2821 (2013.01)

(58) Field of Classification Search
CPC .... A61K 49/04; A61K 49/22; A61K 36/9066; A61K 31/69; C07F 5/02; G01N 33/6896; G01N 2800/2821; G01N 2333/4709; G01N 33/533
USPC .......................................................... 424/9.4
See application file for complete search history.

(56) References Cited

U.S. PATENT DOCUMENTS

| | | |
|---|---|---|
| 5,944,861 A | 8/1999 | MacKenzie et al. |
| 6,391,294 B1 | 5/2002 | Dettmar et al. |
| 2002/0133019 A1 | 9/2002 | Klunk et al. |
| 2003/0149250 A1 | 8/2003 | Kung et al. |
| 2005/0043377 A1 | 2/2005 | Klunk et al. |
| 2006/0002853 A1 | 1/2006 | Kung et al. |
| 2006/0269473 A1 | 11/2006 | Kung et al. |
| 2008/0108840 A1 | 5/2008 | Kung et al. |
| 2008/0154042 A1 | 6/2008 | Klunk et al. |
| 2010/0239496 A1 | 9/2010 | Gangadharmath et al. |
| 2010/0266500 A1 | 10/2010 | Kung et al. |
| 2011/0060138 A1 | 3/2011 | Elmaleh et al. |
| 2011/0208064 A1 | 8/2011 | Chongzhao et al. |
| 2012/0095235 A1 | 4/2012 | Klunk et al. |
| 2012/0183474 A1* | 7/2012 | Ran ...................... C07D 213/02 424/1.89 |
| 2013/0302248 A1 | 11/2013 | Gangadharmath et al. |
| 2013/0315827 A1 | 11/2013 | Elmaleh et al. |
| 2014/0134109 A1 | 5/2014 | Park et al. |
| 2015/0087937 A1 | 3/2015 | Chongzhao et al. |
| 2015/0098903 A1 | 4/2015 | Elmaleh et al. |
| 2015/0190400 A1 | 7/2015 | Klunk et al. |
| 2016/0193363 A1 | 7/2016 | Ran et al. |

FOREIGN PATENT DOCUMENTS

| | | |
|---|---|---|
| GB | 2328443 A | 2/1999 |
| KR | 10-2001-0013726 A | 2/2001 |
| KR | 10-2001-0023065 A | 3/2001 |
| KR | 10-2005-0010058 A | 1/2005 |
| KR | 10-0719456 B1 | 5/2007 |
| KR | 10-2007-0093427 A | 9/2007 |
| KR | 10-2011-0136877 A | 12/2011 |
| KR | 10-1282885 B1 | 7/2013 |
| KR | 10-1478609 B1 | 1/2015 |
| KR | 10-2015-0040644 A | 4/2015 |
| KR | 10-1519354 B1 | 5/2015 |
| KR | 10-2016-0049819 A | 5/2016 |

(Continued)

OTHER PUBLICATIONS

Liu et al. Tetrahedron Lett. 2013, 2070-2073.*

(Continued)

*Primary Examiner* — Michael G. Hartley
*Assistant Examiner* — Sean R Donohue
(74) *Attorney, Agent, or Firm* — Morgan, Lewis & Bockius LLP

(57) ABSTRACT

The present invention relates to a curcumin derivative, a method for producing same, and a photo-acoustic imaging agent comprising the curcumin derivative for detecting beta-amyloid plaque. The curcumin derivative, expressed by chemical formula 1, according to the present invention exhibits superb selective bonding with beta-amyloid, thereby allowing beta-amyloid to be detected by means of an optical or photo-acoustic imaging methods, and, particularly, the curcumin derivative can highly effectively detect photo-acoustic signals with almost no noise by reacting to irradiation of light having a particular wavelength range, and thus can be useful as a composition for detecting beta-amyloid and for diagnosing diseases caused by excessive production of beta-amyloid.

11 Claims, 3 Drawing Sheets

(56) References Cited

FOREIGN PATENT DOCUMENTS

| KR | 20160049819 A | * | 5/2016 | |
|---|---|---|---|---|
| KR | 10-2017-0001045 A | | 1/2017 | |
| WO | 98/57903 A1 | | 12/1998 | |
| WO | 2015/034996 A1 | | 3/2015 | |
| WO | WO-2015034996 A1 | * | 3/2015 | ........... C07D 471/04 |

OTHER PUBLICATIONS

Zhang et al., "Design and Synthesis of Curcumin Analogues for in Vivo Fluorescence Imaging and Inhibiting Copper-Induced Cross-Linking of Amyloid Beta Species in Alzheimer's Disease," Journal of the American Chemical Society, 135: 16397-16409 (2013).

Cui et al., "Smart Near-Infrared Fluorescence Probes with Donor-Acceptor Structure for in Vivo Detection of Beta-Amyloid Deposits," Journal of the American Chemical Society, 136: 3388-3394 (2014).

Blennow et al., "Alzheimer's disease," Lancet 368: 387-403 (2006).

Chiti et al., "Protein Misfolding, Funcational Amyloid, and Human Disease," Annual Review of Biochemistry, 75: 333-366 (2006).

Klunk et al., "Chrysamine-G Binding to Alzheimer and Control Brain: Autopsy Study of a New Amyloid Probe," Neurobiology of Aging, 16: 541-548 (1995).

Cheng et al., "Phase I Clinical Trial of Curcumin, a Chemopreventive Agent, in Patients with High-risk or Pre-malignant Lesions," Aticancer Research, 21: 2895-2900 (2001).

Ran et al., "Design, synthesis, and testing of difluoroboron derivatized curcumins as near infrared probes for in vivo detection of amyloid-beta deposits," Journal of the American Chemical Society, 131: 15257-15261 (2009).

Fu et al., "Highly Sensitive Near-Infrared Fluorophores for in Vivo Detection of Amyloid-Beta Plaques in Alzheimer's Disease," Journal of Medicinal Chemistry, 58: 6972-6983 (2015).

Selkoe, "The Origins of Alzheimer Disease: A is for Amyloid," The Journal of the American Medical Association, 12: 1615-1617 (2000).

Mishra et al., "The effect of curcumin (tumeric) on Alzheimer's disease: An overview," Annals of Indian Academy of Neurology, 11: 13-19 (2008).

Zhang et al., "Near-infrared fluorescence molecular imaging of amyloid beta species and monitoring therapy in animal models of Alzheimer's disease," PNAS, 112: 9734-9739 (2015).

Lee et al., "Neurodegenerative Taupathies: Human Disease and Transgenic Mouse Models," Neuron, 24: 507-510 (1999).

Mathis et al., "A Lipophilic Thioflavin-T Derivative for Positron Emission Tomography (PET) Imaging of Amyloid in Brain," Bioorganic & Medicinal Chemistry Letters, 12: 295-298 (2002).

Lim et al., "The Curry Spice Curcumin Reduces Oxidative Damage and Amyloid Pathology in an Alzheimer Transgenic Mouse," The Journal of Neuroscience, 21: 8370-8377 (2001).

Bai et al., "Syntheses and photophysical properties for BF2 complexes of curcumin analogues," Organic & Biomolecular Chemistry, 12: 1618-1626 (2014).

Liu et al., "BF3-OEt2-Promoted Concise Synthesis of Difluoroboron-Derivatized Curcumins from Aldehydes and 2,4-Pentanedione," Tetrahedron Letters, 54: 2070-2073 (2013).

Klunk et al., "Development of Small Molecule Probes for the Beta-Amyloid Protein of Alzheimer's Disease," Neurobiology of Aging, 15: 691-698 (1994).

Agdeppa et al., "Binding Characteristics of Radiofluorinated 6-Dialkylamino-2-Naphthylethylidene Derivatives as Positron Emission Tomography Imaging Probes for Beta-Amyloid Plaques in Alzheimer's Disease," The Journal of Neuroscience, 21: 1-5 (2001).

Ganguli et al., "Apolipoprotein E Polymorphism and Alzheimer Disease," Archives of Neurology, 57: 824-830 (2000).

Yang et al., "Curcumin Inhibits Formation of Amyloid beta Oligomers and Fibrils, Binds Plaques, and Reduces Amyloid in Vivo," The Journal of Biological Chemistry, 280: 5892-5901 (2005).

International Search Report issued in corresponding International Patent Application No. PCT/KR2016/010878 dated Jun. 27, 2017.

Ginsberg et al., "Molecular Pathology of Alzheimer's Disease and Related Disorders," Cerebral Cortex, 603-654 (1999).

* cited by examiner

[Figure 1]
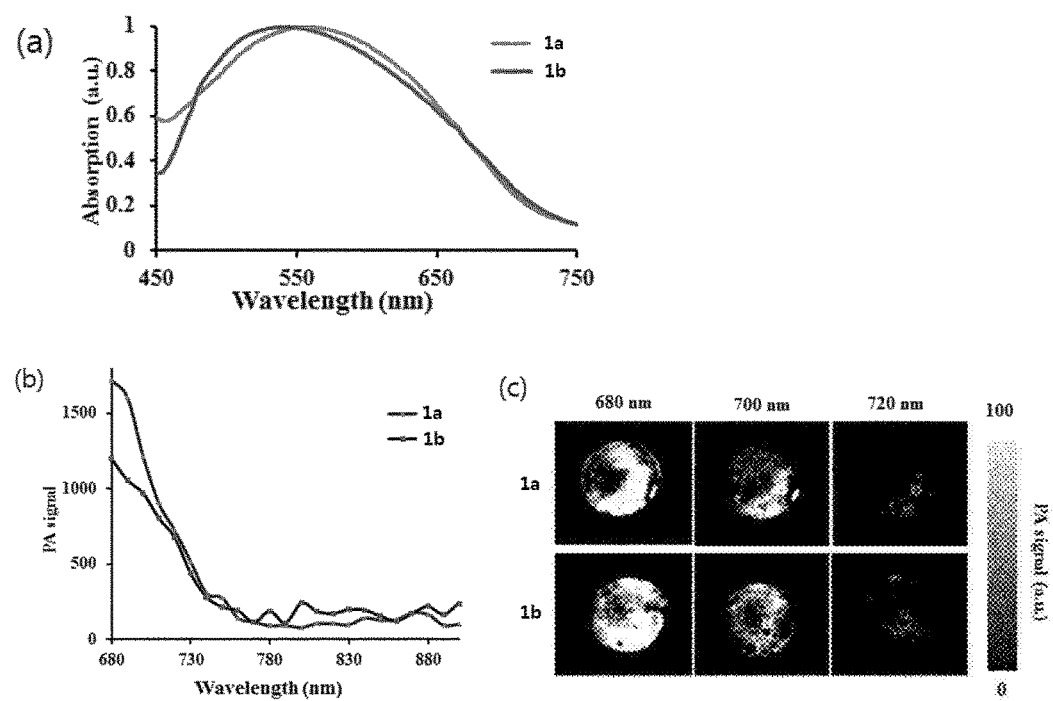

[Figure 2]
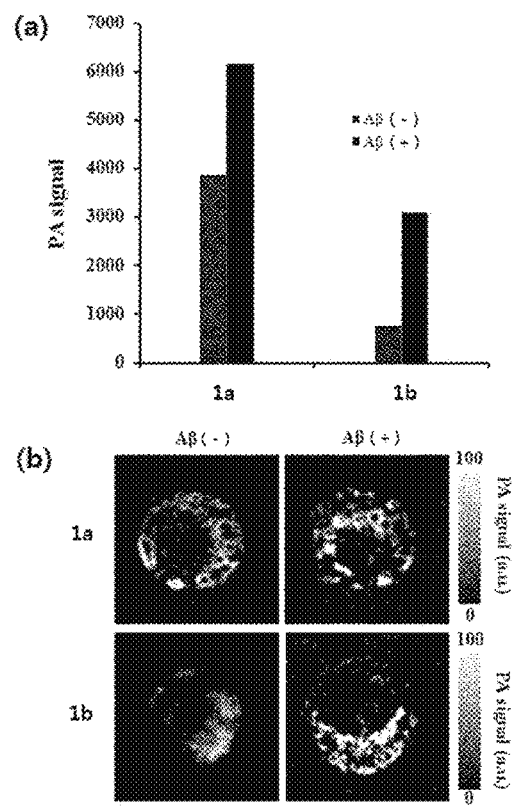
[Figure 3]
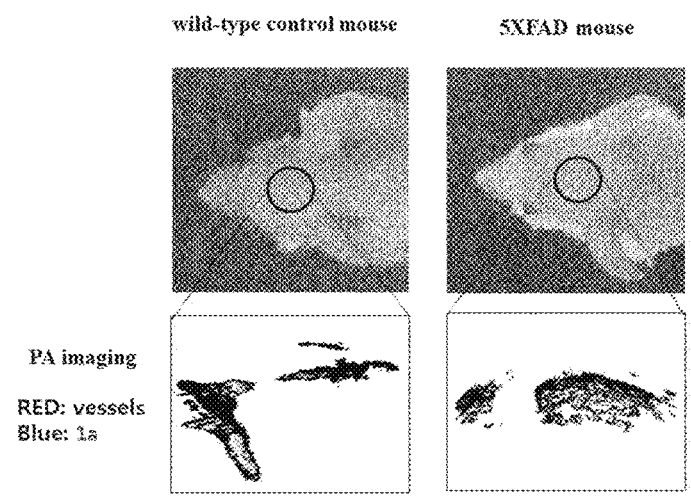

[Figure 4]
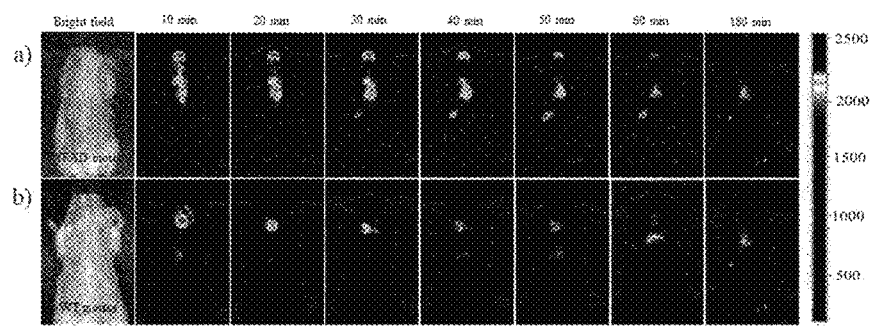
[Figure 5]
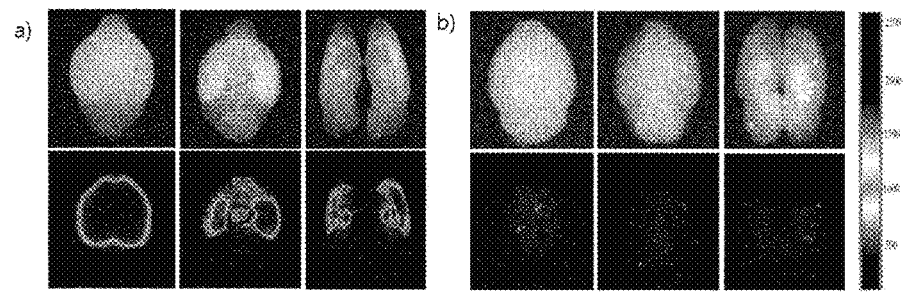

CURCUMIN DERIVATIVE, METHOD FOR PRODUCING SAME, AND PHOTO-ACOUSTIC IMAGING AGENT COMPRISING SAME FOR DETECTING BETA-AMYLOID PLAQUE

TECHNICAL FIELD

The present invention relates to a curcumin derivative, a method for preparing the same, and a photo-acoustic imaging agent for detecting beta-amyloid plaques containing the same.

BACKGROUND ART

With the advancement of modern medicine, the population of elderly people around the world is increasing, and as a result, the number of patients with dementia which is geriatric diseases is increasing rapidly. Alzheimer's disease is the most common form of dementia and is a progressive neurodegenerative disorder characterized by memory loss, cognitive and behavioral stability. Although the cause of the onset of the disease is not clearly known yet, as a result of brain tissue analysis after death, an accumulation of amyloid plaques composed of beta-amyloid peptide (Aβ) between neurons and neurofibrillary tangles formed by hyperphosphorylated tau protein filaments in neurons have been reported [Ginsberg S D et al., Kluwer Academic/Plenum: New York, 1999: pp 603-654; Lee V M et al., Neuron 1999; 24:507-510; Selkoe D J. JAMA 2000; 283: 1615-1617]. 39 to 43 amino acids including the Aβ peptide are derived from the larger amyloid precursor protein (APP). In the production pathway of amyloid, The Aβ peptide is cleaved from APP by sequential proteolysis of β- and γ-secretase. The Aβ peptide is released as a soluble protein and can be detected at low levels in cerebrospinal fluid (CSF) in the normal aged brain. During the course of Alzheimer's disease, it has been found that Aβ peptides are aggregated and form amyloid deposits in the brain or blood vessels [Blennow et al., Lancet. 2006 Jul. 29; 368(9533):387-403]. In addition, it is known that amyloid deposits play a role in amyloidosis where amyloid proteins are abnormally deposited in different organs and/or tissues and cause disease [Chiti et al., Annu Rev Biochem. 2006; 75: 333-66].

Accordingly, for the diagnosis of diseases including Alzheimer's disease that can be diagnosed by quantitatively detecting amyloid aggregates, a number of studies have been conducted on fluorescent compounds that bind well to the beta amyloid aggregate and easily indicate its presence. A representative of these compounds is Congo red (CR), and a definite diagnosis of Alzheimer's disease is possible by performing an autopsy and then staining the brain with the Congo red. However, the Congo red has a disadvantage that it has strong water solubility and cannot pass through the brain blood barrier (BBB), so it cannot enter the brain even if administered to a living person. In addition to the Congo red, one of the first compounds developed is derivatives of Chrysamine-G, but this also was passed through the brain blood barrier at low levels and thus could not actually have been used [Klunk W E, et al., Neurobiol Aging 1994; 15:691-8. Klunk W E, et al., Neurobiol Aging 1995; 16:541-8]. Subsequently, derivatives of 6-dialkylamino-2-naphthylethenylidene (FDDNP) and thioflavin-T (ThT) based derivatives have been developed [Agdeppa E D, et al., J Neuroscience 2001; 21:1-5; Mathis C A, et al., Bioorg Med Chem Lett 2002; 12:295-298.]. In addition, various benzothiazole derivatives and stilbene derivatives have been filed for the patent as a radioisotope labeling compound capable of imaging beta amyloid [US 2002/0133019 A1, US 2003/0149250 A1].

Previously developed fluorescent ligands for the detection of beta amyloid have a complex manufacturing process, have a large molecular weight and did not show significant changes in fluorescence properties after binding to beta amyloid aggregate. In addition, since there was a drawback in that the previously developed fluorescent ligand selectively binds not only specifically to beta amyloid but also to phosphorylated tau protein fibers, they do not have high detection selectivity, but also have low absorption in animal experiments, and it is not easy to remove the ligand from the brain, thus it has been difficult to actually use. Accordingly, there is a continuing need for the development of reagents useful for overcoming the problems of the conventional beta-amyloid detecting ligands and specifically detecting and imaging only amyloid aggregates.

It is known that the curcumin is the main ingredient of curry, an Indian staple food, and the incidence of Alzheimer's disease among Indian elderly people aged 70-79 years is 4.4 times lower than that of Americans [Arch. Neurol. 2000; 57:824-830]. This suggests the potential for the curative effect of curcumin in the prevention and treatment of Alzheimer's disease. In fact, according to recent literature, when curcumin was injected into transgenic mice with amyloid accumulation, the curcumin bound to the plaque through the blood-brain barrier. When curcumin was fed to transgenic mouse, amyloid levels and plaque levels were reduced [J. Biol. Chem. 2005; 18:5892-5901]. Also, the curcumin has been reported to have safety due to low toxicity [J. Neurosci. 2001; 21: 8370-8377; Anticancer Res. 2001; 21: 2895-2900]. Studies have been conducted to predict the effects on the prevention and treatment of dementia in mouse by performing passive avoidance test or Y-maze test in the mouse using curcumin or its derivatives and oleoresin turmeric extract [Korean patent application nos. 2001-0013726 and 2001-0023065]. In addition, new curcumin derivatives such as hydrazinocurcumin have been used for antiangiogenic activity studies [Korean patent application no. 2005-0010058].

Meanwhile, photo-acoustic imaging based on photo-acoustic effects has attracted much attention as a biomedical imaging modality that provides biological information by visualizing intrinsic biological molecules such as melanin and hemoglobin. The high potential of photo-acoustic imaging as biomedical imaging is being accelerated by the development of exogenous contrast agents based on the photo-acoustic response of nanomaterials, in terms of diagnosis and treatment that encompass real-time and targeted imaging with high sensitivity, multi-mode imaging and image-guided therapy.

In this regard, the development of suitable nanoprobes that exhibit photo-acoustic effects is an important technical issue in nanotechnology to improve the efficiency of photo-acoustic imaging and optimize a variety of biomedical applications. Further, the development and artificial manipulation of nanoprobes that exhibit photo-acoustic effects can provide another important insight into the fundamental understanding of photo-acoustic imaging based on nanomaterials. In principle, the photo-acoustic effect is due to the generation of sound waves through the absorption of short-pulsed radiation which locally heat the target, thereby resulting in thermal expansion. Although the extinction coefficient and the conversion efficiency of absorbed photons into heat are the major factors that generate photo-acoustic signals in photo-acoustic imaging based on nanomaterials such as molecular level absorbers, the surface environment of nanomaterials provides another parameter that determines the efficiency of the photo-acoustic effect. Since photo-acoustic effects accompanied by thermal expansion are generated from the locally heated surrounding medium through thermal conversion from nanomaterials to the surrounding medium, the surface environment associated with thermal transfer and divergence dynamics is a sensitive factor that produces photo-acoustic effects based on nanomaterials.

Accordingly, the development and manipulation of new forms of photo-acoustic diagnostic agents for a basic understanding of the photo-acoustic response based on the new photo-acoustic diagnostics can provide important clues for devising and optimizing contrast agents that cause photo-acoustic imaging.

Therefore, the inventors of the present invention have confirmed that the curcumin derivative represented by formula 1 according to the present invention may be useful as a composition for the detection of beta-amyloid and diagnosis of diseases due to excessive production of beta-amyloid, while studying compounds which have excellent selective binding force to beta-amyloid, can be detected by optical imaging or photo-acoustic imaging methods and in particular are capable of detecting high photo-acoustic signals in response to irradiation of light of a particular wavelength range, and have completed the present invention.

DISCLOSURE

Technical Problem

It is an object of the present invention to provide a curcumin derivative or a pharmaceutically acceptable salt thereof.

It is another object of the present invention to provide a method for preparing the curcumin derivative.

It is still another object of the present invention to provide a composition for detection of beta-amyloid plaques comprising the curcumin derivative or a pharmaceutically acceptable salt thereof.

It is further still another object of the present invention to provide a composition for diagnosis of diseases caused by excessive production of beta-amyloid plaques comprising the curcumin derivative or a pharmaceutically acceptable salt thereof.

It is further still another object of the present invention to provide a method for optical imaging detection of beta-amyloid plaques using the curcumin derivative or a pharmaceutically acceptable salt thereof.

It is further still another object of the present invention to provide a method for photo-acoustic imaging detection of beta-amyloid plaques using the curcumin derivative or a pharmaceutically acceptable salt thereof.

Technical Solution

In order to achieve the above objects, the present invention provides the curcumin derivative represented by the following formula 1 or a pharmaceutically acceptable salt thereof:

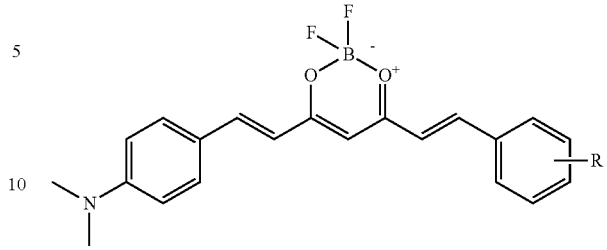

[Formula 1]

wherein R is hydrogen, hydroxy, —B(OH)$_2$, C$_{1-10}$ straight or branched chain alkyl, C$_{1-10}$ straight chain or branched chain alkoxy.

In addition, the present invention provides a method for preparing the curcumin derivative represented by formula 1 comprising the steps of coupling the compound represented by formula 2 and the compound represented by formula 3 in an organic solvent together with a base to obtain the compound represented by formula 4 (step 1); and coupling the compound represented by formula 4 obtained in the step 1 with the compound represented by formula 5 in an organic solvent together with a base to obtain the compound represented by formula 1 (step 2), as shown in reaction scheme 1 below:

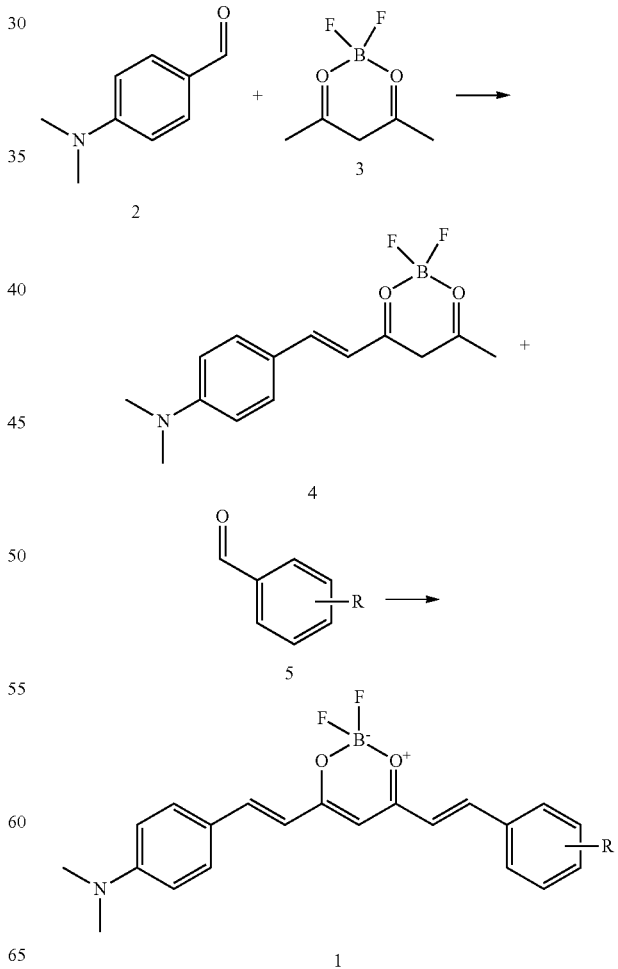

[Reaction Scheme 1]

wherein R is as defined above.

Furthermore, the present invention provides a composition for detection of beta-amyloid plaques comprising the curcumin derivative or a pharmaceutically acceptable salt thereof.

In addition, the present invention provides a composition comprising the curcumin derivative or a pharmaceutically acceptable salt thereof for diagnosis of diseases caused by excessive production of beta-amyloid plaques selected from the group consisting of dementia, Alzheimer's disease, Down's syndrome, amyloid angiopathy, cerebral amyloid angiopathy, systemic amyloidosis, Dutch type amyloidosis, inclusion body myositis, mediterranean fever, Muckle-Wells syndrome, idiopathic myeloma, amyloid polyneuropathy, amyloid cardiomyopathy, systemic senile amyloidosis, hereditary cerebral hemorrhages with amyloidosis, scrapie, Creutzfeld-Jakob disease, kuru, Gerstmann-Straussler-Scheinker syndrome, medullary cercinoma of thyroid, amyotrophy, and Langerhans islet type II diabetes.

In addition, the present invention provides a method for optical imaging detection of beta-amyloid plaques comprising the steps of mixing the curcumin derivative represented by formula 1 or a pharmaceutically acceptable salt thereof with a sample containing the beta-amyloid plaques (step 1); and measuring the fluorescence signal for the beta-amyloid plaques (step 2).

In addition, the present invention provides a method for photo-acoustic imaging detection of beta-amyloid plaques comprising the steps of mixing the curcumin derivative represented by formula 1 or a pharmaceutically acceptable salt thereof with a sample containing the beta-amyloid plaques (step 1); and measuring the photo-acoustic signal for the beta-amyloid plaques (step 2).

Advantageous Effects

Since the curcumin derivative represented by formula 1 according to the present invention has an excellent selective binding force to beta-amyloid and thus can detect beta-amyloid through optical imaging or photo-acoustic imaging methods, and in particular can efficiently detect photo-acoustic signals with high efficiency and with almost no noise in response to irradiation of light of a particular wavelength range, the curcumin derivative may be useful as a composition for beta-amyloid detection and diagnosis of diseases caused by excessive production of beta-amyloid.

DESCRIPTION OF DRAWINGS

FIG. 1a is absorption spectra of the compounds (1a, 1b) of Examples 1 and 2.

FIG. 1b is graphs showing changes in photo-acoustic signals depending on changes in absorption wavelength of the compounds (1a, 1b) of Examples 1 and 2.

FIG. 1c is photo-acoustic images for the compounds (1a, 1b) of Examples 1 and 2 obtained at the absorption wavelengths of 680, 700 and 720 nm, respectively.

FIG. 2a is graphs showing changes in photo-acoustic signals of the compounds (1a, 1b) of Examples 1 and 2 obtained before and after binding to the beta-amyloid aggregates.

FIG. 2b is photo-acoustic images of the compounds (1a, 1b) of Examples 1 and 2 obtained before and after binding to the beta-amyloid aggregates FIG. 3 is a photo-acoustic image for the detection of beta-amyloid obtained after administration of the compound (1a) of Example 1 to a wild-type mouse and a dementia induced mouse (5×FAD mouse).

FIG. 4a is an optical image for the detection of beta-amyloid obtained after administration of the compound (1a) of Example 1 to a dementia induced mouse (5×FAD mouse).

FIG. 4b is an optical image for the detection of beta-amyloid obtained after administration of the compound (1a) of Example 1 to wild-type mouse (WT mouse).

FIG. 5a is an optical image for the detection of beta-amyloid obtained by brain extraction after administration of the compound (1a) of Example 1 to a dementia induced mouse (5×FAD mouse).

FIG. 5b is an optical image for detection of beta-amyloid obtained by brain extraction after administration of the compound (1a) of Example 1 to a wild-type mouse (WT mouse).

BEST MODE

Hereinafter, the present invention will be described in detail.

The present invention provides the curcumin derivative represented by following formula 1 or a pharmaceutically acceptable salt thereof:

[Formula 1]

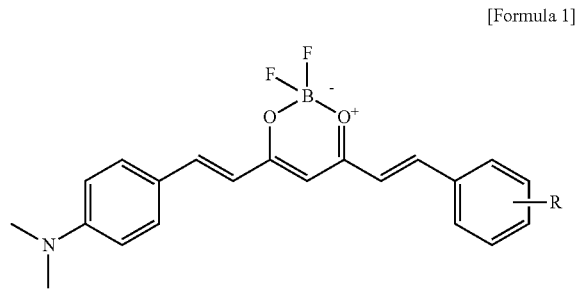

wherein R is hydrogen, hydroxy, —B(OH)$_2$, C$_{1-10}$ straight or branched chain alkyl, C$_{1-10}$ straight chain or branched chain alkoxy.

Preferably, R is hydroxy or —B(OH)$_2$.

More preferably, R is 3-hydroxy or 4-hydroxy.

The chemical structures of the preferred examples of the curcumin derivative represented by formula 1 according to the present invention are summarized in table 1 below.

TABLE 1

| Example | Chemical structure |
|---|---|
| 1 (compound 1a) | 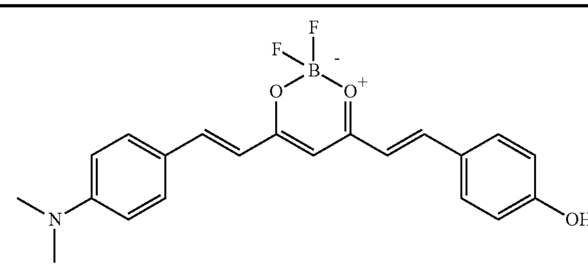 |

TABLE 1-continued

| Example | Chemical structure |
|---|---|
| 2 (compound 1b) | 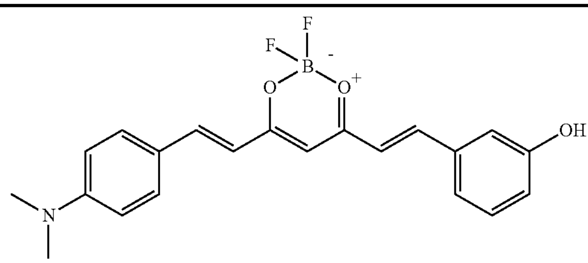 |
| 3 (compound 1c) | 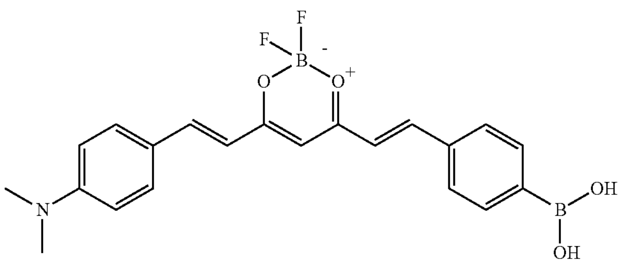 |
| 4 (compound 1d) | 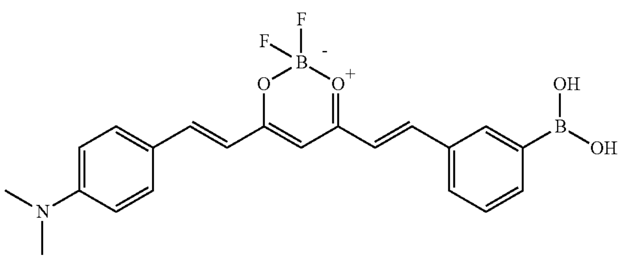 |

The curcumin derivative represented by formula 1 of the present invention can be used in the form of a pharmaceutically acceptable salt, and as the salt, an acid addition salt formed by a pharmaceutically acceptable free acid is useful. Acid addition salts are produced from inorganic acids such as hydrochloric acid, nitric acid, phosphoric acid, sulfuric acid, hydrobromic acid, hydroiodic acid, nitrous acid, phosphorous acid and the like, non-toxic organic acids such as aliphatic mono- and dicarboxylates, phenyl-substituted alkanoates, hydroxy alkanoates and alkane dioates, aromatic acids, aliphatic and aromatic sulfonic acids, and the like, and organic acids such as acetic acid, benzoic acid, citric acid, lactic acid, maleic acid, gluconic acid, methane sulfonic acid, 4-toluenesulfonic acid, tartaric acid, fumaric acid and the like. Examples of such pharmaceutically non-toxic salts include sulfate, pyrosulfate, bisulfate, sulfite, bisulfite, nitrate, phosphate, monohydrogenphosphate, dihydrogenphosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluene sulfonate, chlorobenzenesulfonate, xylenesulfonate, phenyl acetate, phenyl propionate, phenyl butyrate, citrate, lactate, β-hydroxy butyrate, glycolate, malate, tartrate, methanesulfonate, propane sulfonate, naphthalene-1-sulfonate and naphthalene-2-sulfonate and mandelate.

The acid addition salt according to the present invention can be prepared by a conventional method, and for example, can be prepared by dissolving the curcumin derivative represented by formula 1 in an organic solvent such as methanol, ethanol, acetone, dichloromethane, acetonitrile, adding an organic acid or inorganic acid, filtering the resulting precipitate and drying it, or distilling the solvent and excess acid under reduced pressure, followed by drying and then crystallizing in an organic solvent.

In addition, the base can be used to obtain a pharmaceutically acceptable metal salt. The alkali metal or alkaline earth metal salt is obtained, for example, by dissolving the compound in a solution of an excess of alkali metal hydroxide or alkaline earth metal hydroxide, filtering the non-soluble compound salt and evaporating and drying the filtrate. At this time, it is pharmaceutically favorable to prepare sodium, potassium or calcium salt as the metal salt. In addition, the corresponding salt is obtained by reacting an alkali metal or alkaline earth metal salt with a suitable silver salt (e.g., silver nitrate).

In addition, the present invention includes all of the curcumin derivative represented by formula 1 and its pharmaceutically acceptable salts, as well as solvates, hydrates and the like, which can be prepared therefrom.

In addition, the present invention provides a method for preparing the curcumin derivative represented by formula 1 comprising the steps of coupling the compound represented by formula 2 and the compound represented by formula 3 in the first organic solvent to obtain a compound represented by formula 4 (step 1); and coupling the compound represented by formula 4 obtained in the step 1 with the compound represented by formula 5 in the second organic solvent to obtain the compound represented by formula 1 (step 2), as shown in reaction scheme 1 below:

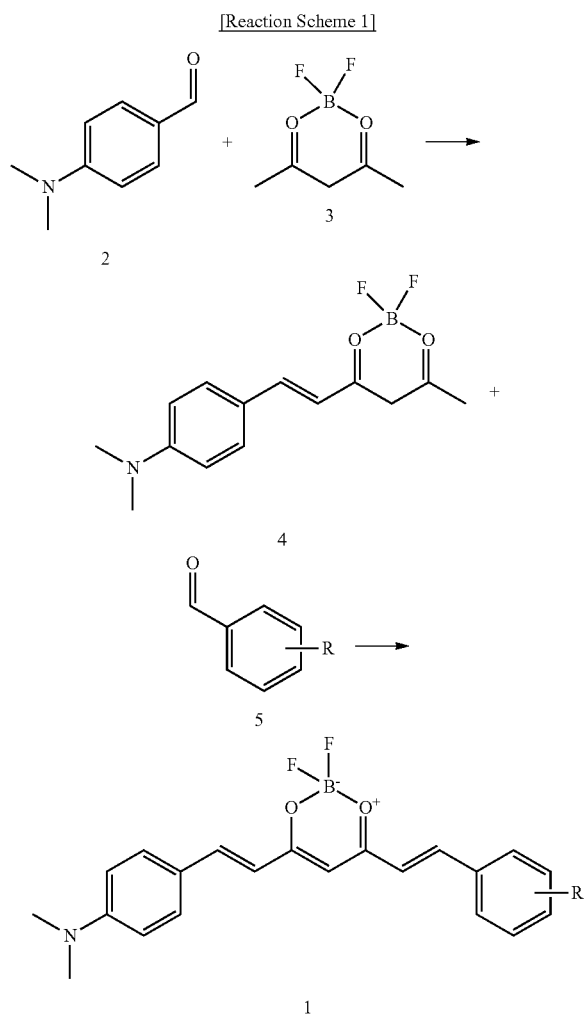

wherein R is the same as defined in the above formula 1.

Hereinafter, the method for preparing the curcumin derivative according to the present invention will be described in detail for each step.

In the preparing method according to the present invention, step 1 is a step of reacting the compound represented by formula 2 and the compound represented by formula 3 together with a base in an organic solvent to obtain the compound represented by formula 4.

In that case, as an organic solvent used in step 1, ethyl acetate, tetrahydrofuran, dioxane, dichloromethane, 1,2-dimethoxyethane, dimethylformamide (DMF), dimethylsulfoxide (DMSO), acetonitrile and the like can be used alone or in combination, and ethyl acetate is preferably used, but not limited thereto.

Also, as a base used in the step 1, n-butylamine, piperidine, potassium hydride, sodium hydride, lithium hydride, lithium hydroxide, sodium hydroxide, potassium hydroxide, cesium hydroxide, rubidium hydroxide, calcium hydroxide and the like can be used, and n-butylamine is preferably used, but not limited thereto.

In addition, the reaction temperature in step 1 may be 0-50° C., preferably 20-30° C., but not limited thereto.

In addition, the reaction time in step 1 may be 1-24 hours, preferably 6-10 hours, but is not limited as long as the reaction proceeds until all of the starting materials disappear.

In the preparing method according to the present invention, step 2 is a step of reacting the compound represented by formula 4 and the compound represented by formula 5 together with a base in an organic solvent to obtain the curcumin derivative represented by formula 1.

In that case, as an organic solvent used in step 2, ethyl acetate, tetrahydrofuran, dioxane, dichloromethane, 1,2-dimethoxyethane, dimethylformamide (DMF), dimethylsulfoxide (DMSO), acetonitrile and the like can be used alone or in combination, and ethyl acetate is preferably used in combination, but not limited thereto.

Also, as a base used in the step 2, n-butylamine, piperidine, potassium hydride, sodium hydride, lithium hydride, lithium hydroxide, sodium hydroxide, potassium hydroxide, cesium hydroxide, rubidium hydroxide, calcium hydroxide and the like can be used, and piperidine is preferably used, but not limited thereto.

In addition, the reaction temperature in step 2 may be 30-120° C., preferably 60-100° C., but not limited thereto.

In addition, the reaction time in step 2 may be 1-24 hours, preferably 6-10 hours, but is not limited as long as the reaction proceeds until all of the starting materials disappear.

Furthermore, the present invention provides a composition for detection of beta-amyloid plaques comprising the curcumin derivative represented by formula 1 or a pharmaceutically acceptable salt thereof.

In addition, the present invention provides a composition for diagnosis of diseases caused by excessive production of beta-amyloid plaques comprising curcumin derivative represented by formula 1 or a pharmaceutically acceptable salt thereof.

The "composition for detection" and "composition for diagnosis" according to the present invention can be used for optical imaging or photo-acoustic imaging methods such as the single photon emission computed tomography (SPECT) or the position emission tomography (PET) and preferably can be used for the photo-acoustic imaging method with high detection efficiency.

The term "photo-acoustic" used in the present invention means a phenomenon, in which a substance absorbs light, thereby locally rising in temperature and this is propagated into the substance as pressure, and is used for the precision spectroscopy because it is possible to measure the absorption of fine light with high sensitivity and it is also possible to measure a sample which is difficult to measure by a general optical method.

The term "photo-acoustic imaging method" used in the present invention refers to a detection or diagnostic method capable of measuring and imaging the photo-acoustic signals using the curcumin derivative represented by formula 1 according to the present invention as a substance exhibiting a photo-acoustic effect wherein the method is a hybrid biomedical imaging modality developed based on the photo-acoustic effect. The photo-acoustic imaging irradiates a non-ionizing laser pulse and the energy delivered by the laser is absorbed by the tissue or contrast agent and converted to heat to cause a transient thermoelastic expansion and further induces the emission of wideband (e.g., MHz) ultrasonic waves. At this time, the generated ultrasonic waves are detected by an ultrasonic transducer to form an image. The emission of the emitted ultrasonic wave, i.e., the intensity of the photo-acoustic signal, is proportional to the local energy deposition. Since the photo-acoustic imaging is a phenomenon generated by absorbing the irradiated light, optical absorption is an important factor for the photo-acoustic imaging. Optical absorption in biological tissues is mediated by intrinsic molecules such as hemoglobin or melanin or by contrast agents introduced from the outside.

The term "beta-amyloid plaque" as used herein refers to the deposited and aggregated state of various insoluble fibrous proteins on the tissues of a patient. The beta-amyloid plaque includes aggregates formed by aggregation of amyloid proteins and/or amyloid deposits formed by an additional combination of amyloid proteins.

In the present invention, "detection of beta-amyloid plaques" or "diagnosis of diseases caused by excessive production of beta-amyloid plaques" is carried out by "bond" between the curcumin derivative represented by formula 1 or a pharmaceutically acceptable salt thereof according to the present invention and amyloid plaques, wherein the "bond" refers to chemical interactions such as covalent bonds, ionic bonds, hydrophilic-hydrophilic interactions, hydrophobic-hydrophobic interactions and complex compound bonds In the present invention, "diseases caused by excessive production of beta-amyloid plaques" may include dementia, Alzheimer's disease, Down's syndrome, amyloid angiopathy, cerebral amyloid angiopathy, systemic amyloidosis, Dutch type amyloidosis, inclusion body myositis, mediteranean fever, Muckle-Wells syndrome, idiopathic myeloma, amyloid polyneuropathy, amyloid cardiomyopathy, systemic senile amyloidosis, hereditary cerebral hemorrhages with amyloidosis, scrapie, Creutzfeld-Jakob disease, kuru, Gerstmann-Straussler-Scheinker syndrome, medullary cercinoma of thyroid, amyotrophy, Langerhans islet type II diabetes and the like.

The composition for diagnosis according to the present invention can be administered orally or parenterally at the time of clinical administration and can be used in the form of a general pharmaceutical preparation. The composition may further comprise a pharmaceutically acceptable carrier or an additive. In the case of formulation, it may be formulated using diluents or excipients such as fillers, fillers, extenders, binders, wetting agents, disintegrants or surfactants generally used, etc.

Accordingly, since the curcumin derivative represented by formula 1 according to the present invention has an excellent selective binding force to beta-amyloid and thus can detect beta-amyloid through optical imaging or photo-acoustic imaging methods, and in particular can efficiently detect photo-acoustic signals with high efficiency and with almost no noise in response to irradiation of light of a particular wavelength range, the curcumin derivative may be useful as a composition for the detection of beta-amyloid and diagnosis of diseases caused by excessive production of beta-amyloid.

The curcumin derivative represented by formula 1 according to the present invention has two chemical structural features. Upon reviewing these features, the first feature is that two aromatic rings at both ends are conjugated, the second feature is that one aromatic ring of these two aromatic rings is substituted with a nitrogen substituent, and the other aromatic ring is substituted with a hydroxy substituent. The inventors of the present invention have found that in the case of compounds that do not have these two chemical structural features, the selective binding force to beta-amyloid is significantly reduced.

Specifically, as a result of photographing the optical-image and photo-acoustic-image using the compounds according to the present invention and the comparative compounds which have no the above two chemical structural features, it was realized that although the administration concentration of the compound according to the present invention was significantly lower than that of the comparative compound, the results of the imaging were clearer in the case of the present invention.

Therefore, the inventors of the present invention expect that the two chemical structural features significantly improve the selective binding force to beta-amyloid.

Another aspect of the present invention can provide a method for detecting a beta-amyloid using the curcumin derivative represented by formula 1 or a pharmaceutically acceptable salt thereof.

The present invention provides a method for the detection of an optical image of beta-amyloid plaques comprising the steps of mixing the curcumin derivative represented by formula 1 or a pharmaceutically acceptable salt thereof with a sample containing the beta-amyloid plaques (step 1); and measuring the fluorescence signals for the beta-amyloid plaques (step 2).

In addition, the present invention provides a method for the detection of a photo-acoustic image of beta-amyloid plaques comprising the steps of mixing the curcumin derivative represented by formula 1 or a pharmaceutically acceptable salt thereof with a sample containing the beta-amyloid plaques (step 1); and measuring the photo-acoustic signals for the beta-amyloid plaques (step 2).

In that case, the curcumin derivative represented by formula 1 or a pharmaceutically acceptable salt thereof according to the present invention exhibits a high binding affinity for the beta-amyloid plaque and thus forms a specific binding.

The step of administering the composition to a subject can be effected by introducing a detectable amount of a composition comprising the curcumin derivative or a pharmaceutically acceptable salt thereof according to the present invention into the tissue or the subject. The introduction into the tissue or the subject is administered to the tissue or the subject by methods known to those skilled in the art.

The term "tissue" refers to a portion of a subject's body. Examples of tissues may include the brain, heart, liver, blood vessels, and arteries. The "detectable amount" is an amount of composition needed to be detected by the selected detection method. The amount of composition introduced into a patient to be detected can be readily determined by one skilled in the art. For example, the composition can be administered to the subject while increasing the amount of composition until the active ingredient in the composition is detected by the selected detection method. The term "subject" means a human or other animal. Those skilled in the art can easily determine the time required for the curcumin derivative according to the present invention to bind to the amyloid aggregate by introducing the composition into the subject in a detectable amount and then detecting the label at various time points after administration.

Administration of the compositions of the present invention into a subject can be performed by a systemic or local route of administration. For example, the composition may be administered orally, rectally, parenterally (intravenously, intramuscularly or subcutaneously), intracisternally, intravaginally, intraperitoneally, intravesically, topically (powder, ointment or drip), or in a buccal or intranasal spray. The composition can be administered to a subject so that it can move through the body. In addition, the composition may be administered to a particular organ or tissue of interest.

In the method of detecting beta amyloid aggregate of the present invention, the composition comprising the curcumin derivative or a pharmaceutically acceptable salt thereof is introduced into the subject in a detectable amount, and the fluorescent label can be detected non-invasively in the subject after sufficient time for the compound to bind to the amyloid aggregate. Alternatively, a tissue sample is separated from the subject and the composition is introduced into the tissue sample, and then the fluorescent label can be detected after sufficient time for the curcumin derivative in the composition to bind to the amyloid aggregate. The step of detecting the fluorescent label may be performed using optical imaging or photo-acoustic imaging methods such as single photon emission computed tomography (SPECT) or positron emission tomography (PET) which is an in-vivo nuclear medical analytical method, and particularly can be accomplished by the photo-acoustic imaging method which has a very high detection efficiency.

Imaging beta-amyloid plaques in the brain has several potential advantages. Imaging techniques can improve diagnostic methods by identifying a potential patient who has an excessive amount of beta-amyloid plaques accumulated in the brain, and thus is likely to develop Alzheimer's disease. The technique will also be useful for monitoring the progression of Alzheimer's disease. Once anti-beta amyloid drug therapy is available, the imaging of beta-amyloid plaques in the brain can provide an important means of monitoring therapy.

The reason that it is difficult to perform the imaging of beta-amyloid plaque directly in vivo is because the plaque has many of the same physical properties as normal tissue, such as density and moisture content. For this reason, attempts to image the beta-amyloid plaques using magnetic resonance imaging (MRI) and computerized axial tomography (CAT) have shown disappointing results, and efforts to label the beta-amyloid plaques with antibodies, serum amyloid P proteins, or other probe molecules provided some selectivity for the perimeter of the tissue, but in case for the inside of the tissue, provided only bad images.

However, the curcumin derivative represented by formula 1 of the present invention can be imaged using fluorescence characteristic alone or photo-acoustic characteristics even without using a radioisotope, and also can detect the beta-amyloid plaque with high sensitivity by using the difference in fluorescence characteristics before and after binding to the beta-amyloid plaque.

Hereinafter, the present invention will be described in more detail with reference to the following Examples. However, it should be noted that the following examples are illustrative of the present invention only and are not intended to limit the scope of the present invention.

Examples 1-4: Preparation of Compound 1a (R=4-OH), Compound 1b (R=3-OH), Compound 1c (R=4-B(OH)$_2$) and Compound 1d (R=3-B(OH)$_2$)

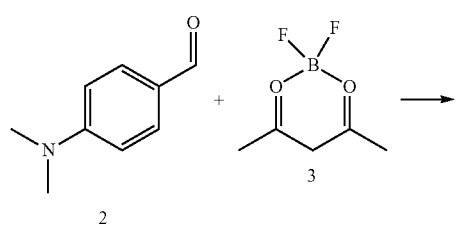

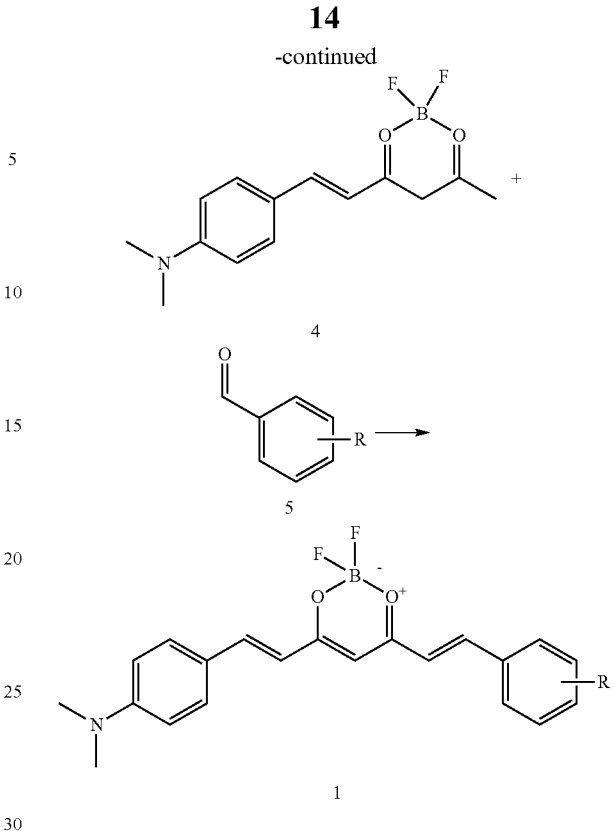

The compound 2 (0.5 g, 3.2 mmol) and the corresponding compound 3 (0.5 g, 3.2 mmol) were dissolved in ethyl acetate (50 ml), and n-butylamine (0.11 g, 1.6 mmol) was added at 0° C. The reaction mixture was stirred at room temperature for 8 hours until the starting materials disappeared. The solution was extracted with ethyl acetate, washed with water and dried over MgSO$_4$. The solvent was evaporated in vacuo and the residue was chromatographed (SiO$_2$, EtOAc/n-hexane=3/7 (v/v)) to give compound 4 (0.55 g, 62%).

Next, the prepared compound 4 (0.1 g, 0.36 mmol) and the corresponding aldehyde (compound 1a=4-hydroxyl benzaldehyde; compound 1b=3-hydroxyl benzaldehyde; compound 1c=4-formylphenyl boronic acid; compound 1d=3-formylphenyl boronic acid) (Sigma-Aldrich (St. Louis, Mo., USA)) was dissolved in ethyl acetate (50 ml) and piperidine (30 mg, 0.36 mmol) was added at 0° C. The reaction mixture was stirred at 80° C. for 8 hours until the starting materials disappeared. The solution was extracted with ethyl acetate, washed with water and dried over MgSO$_4$. The solvent was evaporated in vacuo and the residue was chromatographed (SiO$_2$, EtOAc/n-hexane=1/1 (v/v)) to give compounds 1a and 1b (1a: 37%), (1b: 32%), (1c: 41%), (1d: 38%).

Example 1 (Compound 1a)

$^1$H NMR (500 MHz, Aceton-d6): 3.09 (6H, s), 6.24 ($^1$H, s), 6.73 ($^1$H, d, J=15.3 Hz), 6.78 (2H, d, J=8.4 Hz), 6.82 ($^1$H, d, J=16.0 Hz), 6.92 (2H, d, J=8.4 Hz), 7.65-7.67 (4H, m), 7.83 ($^1$H, d, J=16.0 Hz), 7.94 ($^1$H, d, J=15.3 Hz);
$^{13}$C NMR (125 MHz, CDCl$_3$, d, ppm): 39.3, 101.0, 112.0, 114.5, 116.2, 118.4, 122.1, 126.5, 131.3, 132.0, 144.6, 147.9, 153.5, 160.9, 177.6, 179.9.

Example 2 (Compound 1b)

$^1$H NMR (500 MHz, Aceton-d6): 3.09 (6H, s), 6.31 ($^1$H, s), 6.75 ($^1$H, d, J=15.3 Hz), 6.79 (2H, d, J=9.1 Hz), 6.92-6.95

(2H, m), 7.20-7.27 (3H, m), 7.69 (2H, d, J=9.1 Hz), 7.77 ($^1$H, d, J=16.0 Hz), 7.99 ($^1$H, d, J=15.3 Hz), 8.68 ($^1$H, OH);

$^{13}$C NMR (125 MHz, CDCl$_3$, d, ppm): 39.3, 101.5, 112.1, 114.1, 115.1, 118.4, 120.5, 121.9, 122.0, 130.2, 132.4, 136.2, 143.7, 149.0, 153.8, 158.0, 176.6, 180.9.

Example 3 (Compound 1c)

$^1$H NMR (500 MHz, Aceton-d6): 3.11 (6H, s), 6.34 ($^1$H, s), 6.76 ($^1$H, d, J=15.3 Hz), 6.79 (2H, d, J=8.4 Hz), 7.06 ($^1$H, d, J=15.3 Hz), 7.30 (2H, s), 7.69 (2H, d, J=8.4 Hz), 7.73 (2H, d, J=7.65 Hz), 7.86 ($^1$H, d, J=15.3 Hz), 7.93 (2H, d, J=7.65 Hz), 8.01 ($^1$H, d, J=15.3 Hz);

$^{13}$C NMR (125 MHz, CDCl$_3$, d, ppm): 39.3, 101.6, 112.1, 114.1, 121.9, 122.4, 127.9, 132.5, 134.8, 136.4, 143.5, 149.2, 153.8, 176.5, 180.9.

Example 4 (Compound 1d)

$^1$H NMR (500 MHz, Aceton-d6): 3.10 (6H, s), 6.31 ($^1$H, s), 6.75 ($^1$H, d, J=15.3 Hz), 6.79 (2H, d, J=9.2 Hz), 7.02 ($^1$H, d, J=15.3 Hz), 7.34 (2H, s), 7.45 ($^1$H, dd, J=7.5 Hz), 7.68 (2H, d, 9.2 Hz), 7.81 ($^1$H, d, J=8.4 Hz), 7.87 ($^1$H, d, J=15.3 Hz), 7.93 ($^1$H, d, J=7.5 Hz), 7.99 ($^1$H, d, J=15.3 Hz), 8.23 ($^1$H, s);

$^{13}$C NMR (125 MHz, CDCl$_3$, d, ppm): 39.3, 101.4, 112.1, 114.1, 121.6, 121.9, 128.4, 130.9, 132.4, 133.9, 134.4, 136.8, 144.0, 149.0, 153.7, 176.7, 180.8.

Experimental Example 1: Evaluation of Amplification of Photo-Acoustic Signal of Curcumin Derivative for Detection of Amyloid Plaques (1) Preparation of Aβ42 Fibril Aβ 42 (rPeptide (Bogart, Ga., 30622)) as Aβ peptide was dissolved in a pH 7.4 PBS buffer solution in a final concentration of 100 μM and then stirred at room temperature for 3 days using a magnetic bar at 1200 rpm. The formation of Aβ fibril was confirmed by the ThT (Thioflavin T) assay (2) Absorption Spectra of Curcumin Derivatives (1a and 1b) of Examples 1 and 2 (FIG. 1a)

The maximum excitation wavelengths of the two curcumin derivative compounds of Examples 1 and 2 according to the present invention were measured with SpectraMax M2 (Molecular Devices). 100 μM of curcumin derivative 1a and 1b compounds of Examples 1 and 2 were used as final concentrations using a PBS buffer solution. As a result, all of the two curcumin derivatives showed an absorption wavelength at 450-750 nm (FIG. 1a).

(3) The Photo-Acoustic Signals of Curcumin Derivatives (1a and 1b) of Examples 1 and 2 (FIGS. 1b and 1c)

100 μM of curcumin derivatives 1a and 1b compounds of Examples 1 and 2 were used as final concentrations. Measurements of photo-acoustic signals at 680-900 nm showed the strongest acoustic signal at 680 nm (FIGS. 1b and 1c). FIG. 1b is a photograph showing changes in photo-acoustic signals depending on changes in absorption wavelengths, and FIG. 1c shows changes in photo-acoustic images depending on changes in wavelengths of 680, 700 and 720 nm.

(4) Amplification of Photo-Acoustic Signals of Curcumin Derivatives (1a, 1b) of Examples 1 and 2 for Detection of Amyloid Plaques (FIGS. 2a and 2b)

This experiment is the result of in-vitro studies of photo-acoustic changes of two curcumin derivatives of Examples 1 and 2 bound to the beta-amyloid aggregate. Amplification of the acoustic signals after combining with 100 μM curcumin derivative (1a, 1b) was measured using 100 μM of cohesive Aβ42 peptide. The amplification of photo-acoustic signals was closely related to their physical agglomeration. When the curcumin derivative binds to the Aβ42 aggregate, a single molecule does not bind to the Aβ42 aggregate, but many curcumin derivatives bind to the Aβ42 aggregate. This leads to the physical aggregation of curcumin derivatives and thus leads to the amplification of photo-acoustic signals. As a result of the experiments in the present invention, amplification of the photo-acoustic signals was confirmed in the case of the curcumin derivatives bound to the Aβ42 aggregate, not in the case of the curcumin derivatives not bound to the Aβ42 aggregate (FIGS. 2a and 2b). FIG. 2a is graphs showing changes in photo-acoustic signals of the curcumin derivatives (1a, 1b) before and after binding to the beta-amyloid aggregates. FIG. 2b compares photo-acoustic images before and after binding to the beta-amyloid aggregates Experimental Example 2: In Vivo Photo-Acoustic Imaging Experiments with Mouse in Alzheimer's Disease Model Using the Curcumin Derivative (1a, 1b) Compounds of Examples 1 and 2

(1) A Comparative Experiment of Photo-Acoustic Imaging for Detection of Beta Amyloid in Wild-Type Mouse and Dementia-Induced Mouse Using Compound (1a) of Example 1 (FIG. 3)

Into the tail vein of 13-month-old demented-induced mouse (5×FAD mouse) and wild-type control mouse, compound 1a (400 μg/kg) of Example 1 was injected, and after 30 minutes, photo-acoustic imaging was performed. As shown in FIG. 3, After intravenous injection into the wild-type control mouse, the signal of compound 1a of Example 1 was not detected in the mouse brain. However, after intravenous injection into the dementia-induced mouse, the signal of beta amyloid plaques present in the mouse brain was observed (FIG. 3). This result confirms that the compound (1a) of Example 1 binds to the beta-amyloid aggregate and shows a high photo-acoustic signal.

Experimental Example 3: In Vivo Optical Imaging Experiments with Mouse in Alzheimer's Disease Model Using the Curcumin Derivative (1a, 1b) Compounds of Examples 1 and 2

(1) Comparative Experiment of Optical Imaging for Detection of Beta Amyloid in Wild-Type Mouse and Dementia-Induced Mouse Using Compound (1a) of Example 1 (FIG. 4).

The curcumin derivative developed by the present invention can be used not only as a photo-acoustic diagnostic agent but also as an optical diagnostic agent. After injecting compound 1a (400 μg/kg) of Example 1 into the tail vein of 13-month old dementia-induced mice (5×FAD mouse) and wild type mouse (WT mouse), optical imaging was performed for 10-180 minutes. FIG. 4a shows the results of experiments on dementia-induced mouse, and FIG. 4b shows experimental results on wild-type mouse. As shown in FIG. 4, after intravenous injection into a wild-type mouse, it was revealed that the signal of compound (1a) of Example 1 rapidly disappeared in the brain of the mouse, and after intravenous injection into the dementia-induced mouse, it was possible to identify the beta-amyloid aggregates present across the brain of the mouse. This result confirms that the compound (1a) of Example 1 binds to the beta-amyloid aggregate and shows a high optical signal.

(2) Comparative Experiment of Optical Imaging for Detection of Beta Amyloid in the Brain of Wild-Type Mouse and Dementia-Induced Mouse Using Compound (1a) in Example 1 (FIG. 5).

In order to evaluate the beta-amyloid binding activity of the curcumin derivative in the brain of a living mouse, which has been developed as a photo-acoustic and optical diagnostic agent, the compound (1a) (400 μg/kg) of Example 1 was injected into the tail vein of a 13-month old dementia-induced and wild type mouse, and after 30 minutes, the brain of the mouse was extracted and the optical imaging was performed (FIG. 5). FIG. 5a shows the results of experiments on dementia-induced mouse, and FIG. 5b shows experimental results on wild-type mouse. As shown in FIG. 5, it was possible to identify a strong optical signal by the compound (1a) of Example 1 in the mouse brain, and when the central part of the brain was cut and observed, a strong signal by the curcumin derivative (1a) of Example 1 was confirmed in the cerebral cortex. This result confirms that the compound (1a) of Example 1 binds to the beta-amyloid aggregate and shows a high optical signal.

The invention claimed is:

1. A curcumin derivative represented by the following formula 1 or a pharmaceutically acceptable salt thereof:

[Formula 1]

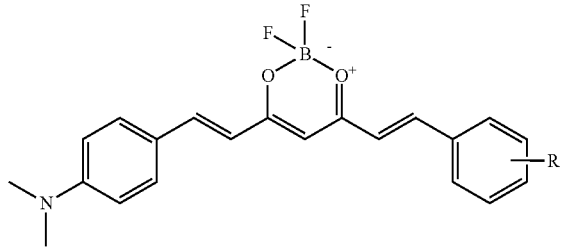

wherein R is —B(OH)$_2$.

2. A method for preparing a curcumin derivative represented by formula 1 comprising the steps of coupling the compound represented by formula 2 and the compound represented by formula 3 in an organic solvent together with a base to obtain the compound represented by formula 4; and coupling the compound represented by formula 4 obtained in the coupling and the compound represented by formula 5 in an organic solvent together with a base to obtain the compound represented by formula 1, as shown in reaction scheme 1 below:

[Reaction Scheme 1]

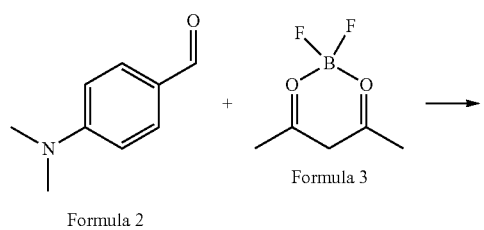

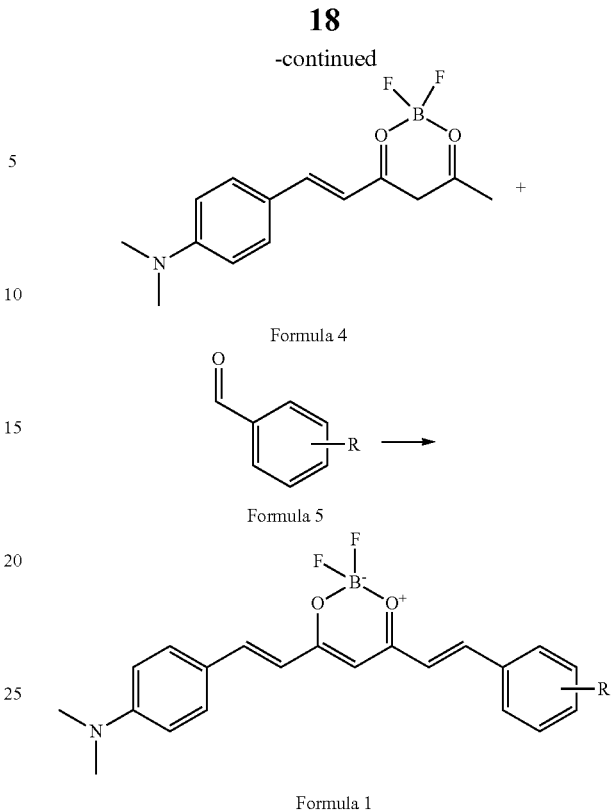

wherein R is as defined in claim 1.

3. A composition for the detection of beta-amyloid plaque comprising the curcumin derivative or the pharmaceutically acceptable salt thereof according to claim 1.

4. A composition for the detection of beta-amyloid plaque according to claim 3, characterized in that the composition for the detection is used in optical imaging or photo-acoustic imaging methods.

5. A composition for the diagnosis of diseases by excessive production of beta-amyloid plaque comprising the curcumin derivative or the pharmaceutically acceptable salt thereof according to claim 1.

6. The composition for the diagnosis according to claim 5, characterized in that the diseases by excessive production of beta-amyloid plaque are selected from the group consisting of dementia, Alzheimer's disease, Down's syndrome, amyloid angiopathy, cerebral amyloid angiopathy, systemic amyloidosis, Dutch type amyloidosis, inclusion body myositis, mediteranean fever, Muckle-Wells syndrome, idiopathic myeloma, amyloid polyneuropathy, amyloid cardiomyopathy, systemic senile amyloidosis, hereditary cerebral hemorrhages with amyloidosis, scrapie, Creutzfeld-Jakob disease, kuru, Gerstmann-Straussler-Scheinker syndrome, medullary cercinoma of thyroid, amyotrophy, and Langerhans islet type II diabetes.

7. The composition for the diagnosis according to claim 5, characterized in that the composition for the diagnosis is used in optical imaging or photo-acoustic imaging methods.

8. A method for optical imaging detection of beta-amyloid plaques comprising the steps of mixing the curcumin derivative or the pharmaceutically acceptable salt thereof of claim 1 with a sample containing the beta-amyloid plaques; and measuring the fluorescence signals for the beta-amyloid plaques.

9. A method for photo-acoustic imaging detection of beta-amyloid plaques comprising the steps of mixing the curcumin derivative or the pharmaceutically acceptable salt thereof of claim 1 with a sample containing the beta-amyloid plaques; and measuring the photo-acoustic signals for the beta-amyloid plaques.

10. The curcumin derivative or the pharmaceutically acceptable salt thereof according to claim 1, wherein the curcumin derivative represented by the formula 1 is below:

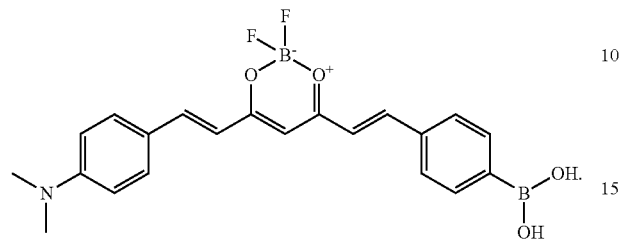

11. The curcumin derivative or the pharmaceutically acceptable salt thereof according to claim 1, wherein the curcumin derivative represented by the formula 1 is below:

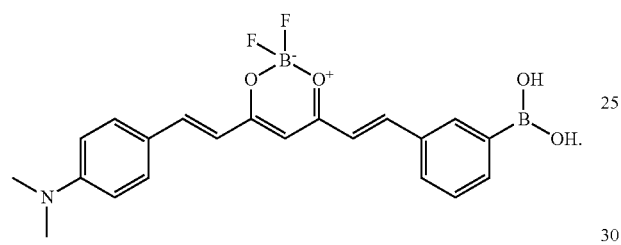

* * * * *